United States Patent

Baumert

[11] 4,098,128
[45] Jul. 4, 1978

[54] METHOD OF AND APPARATUS FOR MONITORING SLAG THICKNESS IN REFINING CRUCIBLE

[75] Inventor: Jean Baumert, Esch, Alzette, Luxembourg

[73] Assignee: ARBED — Aciériés Reunies de Burbach-Eich-Dudelange S.A., Luxembourg, Luxembourg

[21] Appl. No.: 626,871

[22] Filed: Oct. 29, 1975

[30] Foreign Application Priority Data

Oct. 31, 1974 [LU] Luxembourg ............................ 71228

[51] Int. Cl.² ...................... G01N 29/00; G01F 23/28
[52] U.S. Cl. ..................................... 73/591; 73/290 V
[58] Field of Search ................... 73/67, 67.2, 69, 71.4, 73/290 V, 290 B, 552, 555, 557, 561

[56] References Cited

U.S. PATENT DOCUMENTS

| | | | |
|---|---|---|---|
| 3,237,451 | 3/1966 | Haeff | 73/290 V X |
| 3,240,674 | 3/1966 | Ledwidge | 73/69 X |
| 3,603,149 | 9/1971 | McKown | 73/290 V |
| 3,782,180 | 1/1974 | Harris | 73/69 |
| 3,807,222 | 4/1974 | Eggers | 73/67.2 |
| 3,910,116 | 10/1975 | Smith | 73/290 V |
| 3,913,407 | 10/1975 | Hanff et al. | 73/552 |
| 3,927,569 | 12/1975 | Bergdahl et al. | 73/290 V |

FOREIGN PATENT DOCUMENTS

1,191,595  4/1965  Fed. Rep. of Germany ......... 73/555

*Primary Examiner*—Richard C. Queisser
*Assistant Examiner*—John S. Appleman
*Attorney, Agent, or Firm*—Karl F. Ross

[57] ABSTRACT

An acoustic tube having several resonant frequencies is directed into the mouth of a rafining crucible and is heated to above 100° C. A microphone at the remote end of this tube receives sound passing through the tube and generates an electrical output corresponding to the sound received. This electrical output is linearized over a band width including several of the resonant frequencies of the tube and the signal is then passed through a low pass filter to eliminate parasitic oscillations and through a mixer where it is combined with a signal from a local oscillator. The intermediate-frequency signal thus produced is passed through either of a pair of band-pass filters and is displayed. The signal strength at the output is inversely proportional to the depth of slag in the crucible, as the deeper the slag the more sound is absorbed in the crucible.

15 Claims, 3 Drawing Figures

METHOD OF AND APPARATUS FOR MONITORING SLAG THICKNESS IN REFINING CRUCIBLE

FIELD OF THE INVENTION

The present invention relates to the monitoring of a refining operation. More particularly this invention concerns a method of and an apparatus for acoustically monitoring the depth of the slag on the melt in a refining crucible.

BACKGROUND OF THE INVENTION

In the oxygen refining of pig iron it is necessary to monitor how full the refining crucible is. In particular it is useful to know the thickness of the slag layer that forms on top of the melt during the refining operation.

It has been found that a convenient method of determining this slag thickness is by monitoring the noise produced by the oxygen jet directed at the melt. To this end a microphone is mounted near the top of the crucible and detected sound is transformed into an electrical signal whose intensity readily can be measured. In order to achieve the most advantageous ratio between useful and parasitic noises and in order to minimize distortions it is necessary to have the microphone as close as possible to the mouth of the crucible.

It is therefore necessary to provide a cooling system for the microphone. This is typically done by means of water-filled coolant tubes surrounding the microphone. A considerable disadvantage of this system is that the extreme heat frequently causes the water in the coolant to boil, thereby greatly increasing the extraneous noise level. Furthermore, the microphone invariably has a very limited service life due to its location close to the hot refining crucible.

OBJECTS OF THE INVENTION

It is therefore an object of the present invention to provide an improved method of and a system for refining steel.

Another object is the provision of an improved acoustic monitoring method and apparatus for determining how full a refining crucible is and, more particularly, for determining the thickness of the slag layer on the melt in the crucible.

Yet another object is the provision of such an acoustic monitoring system which has a long service life and wherein the ratio of useful to extraneous noise is kept at a maximum.

SUMMARY OF THE INVENTION

These objects are attained according to the present invention in a refining monitoring system wherein the microphone that converts the sound detected into an electrical signal is provided at the remote end of an acoustic tube directed at the melt and maintained at a temperature substantially above ambient temperature, and the electrical signal produced by the microphone, which is non-linear due to the resonant frequencies of the tube, is linearized and then passed through a heterodyne-type electronic circuit for producing an output corresponding to the noise level on the surface of the melt.

The microphone, which in accordance with the present invention may be the condenser type, is mounted at the relatively cool extremity of the acoustic tube, which in accordance with this invention is made of copper and is substantially straight. The output of the microphone is linearized to compensate for the standing wave produced in the tube as well as the variation of resonant frequency which is caused by the temperature of the column of air in the tube. Thus this tube is heated up to a temperature substantially higher than the ambient temperature, at least 100° C. Since there is no cooling by means of water parasitic noise due to the flow of water through the coolant tubes and boiling of the water in the cooling tubes is eliminated completely and a reference temperature is obtained for compensating the frequency response of the probe.

The invention exploits the phenomenon of resonance of the acoustic device constituted by the crucible and the stack over it. This characteristic frequency is determined principally by the dimensions of the crucible and of the stack, the level to which the crucible is filled with the melt, and the gas temperature during the oxygen blowing. It varies slightly as the refractory lining of the crucible wears. Nonetheless the useful range differs from one refinery to another, but can usually be found between 150 Hz and 250 Hz. The range is generally less than 100 Hz. The intensity of the noises produced is a direct function of the depth of the slag floating on the melt, as this slag has a considerable sound-damping effect. Therefore once the appropriate characteristic frequency of the crucible-stack system is obtained the noise intensity at this frequency will give a good indication of the slag depth, the process parameter of particular interest in a refining operation.

The frequency response of the acoustic pipe or tube with the microphone is determined at the manufacturing plant for this probe in an acoustically closed chamber and the filter is then adjusted for the particular tube. This filter is, however, adjusted so as to allow the tube itself to be used across the entire frequency band likely to be employed at the site, usually between 100 Hz and 250 Hz. This frequency band typically includes several resonant frequencies or standing waves which can be formed in the tube.

In accordance with a further feature of this invention the linearized and filtered signal is fed through a band-pass filter which is adjusted to let through only those signals having a frequency corresponding to the characteristic frequency of the crucible in question. The intensity, or more accurately the sound-damping, of this signal is a measure of the depth of the slag floating on the melt. Thus with the system according to the present invention it is necessary to examine the spectrum of sound emitted by the crucible with which the electro-acoustic probe is to be used in order to determine just what frequency band is to be monitored.

According to yet another feature of this invention is low-frequency superheterodyne system is used. The band-pass filter has a band width of, for example, 60 Hz. The local oscillator and the band-pass filter are made adjustable so as to allow the system to be readjusted in case the operating conditions are changed, as changed operating conditions change the characteristic frequency of the crucible. Thus in accordance with the present invention the system is tuned up for each refining operation, although it is not necessary to retune during the operation.

In order to avoid overly frequent changing of the local-oscillator frequency in accordance with the present invention a band-pass filter having a fixed band width 100 Hz is used, which gives an adequate signal/noise ratio. Such a filter makes the apparatus insensitive to minor variations in the characteristic frequency of the crucible. It also lies within the scope of this invention to provide a band-pass filter having a band width of 5 Hz so as to be able to use the device as a frequency analyzer. With such a system the useful or parasitic noise is recorded by means of a tape recorder or the like and then played through the system in order to analyze the various parts of the noise spectrum.

With the system according to the present invention a high degree of accuracy is obtained because only useful frequencies are analyzed. The apparatus may use a relatively fragile sound pickup, for example a condenser microphone, while maintaining a long service life, in practice more than a year. In addition the apparatus can be adapted for use with any type of metallurgical crucible. It is easy to use and does not require any special extra devices for proper adjustment. In addition the output will always be substantially the same so that it will be possible to obtain extremely accurate readings for proper refining of pig iron.

BRIEF DESCRIPTION OF THE DRAWING

The above and other objects, features, and advantages of the invention will become more readily apparent from the following description, reference being made to the accompanying drawing in which.

SPECIFIC DESCRIPTION

Figure 1:
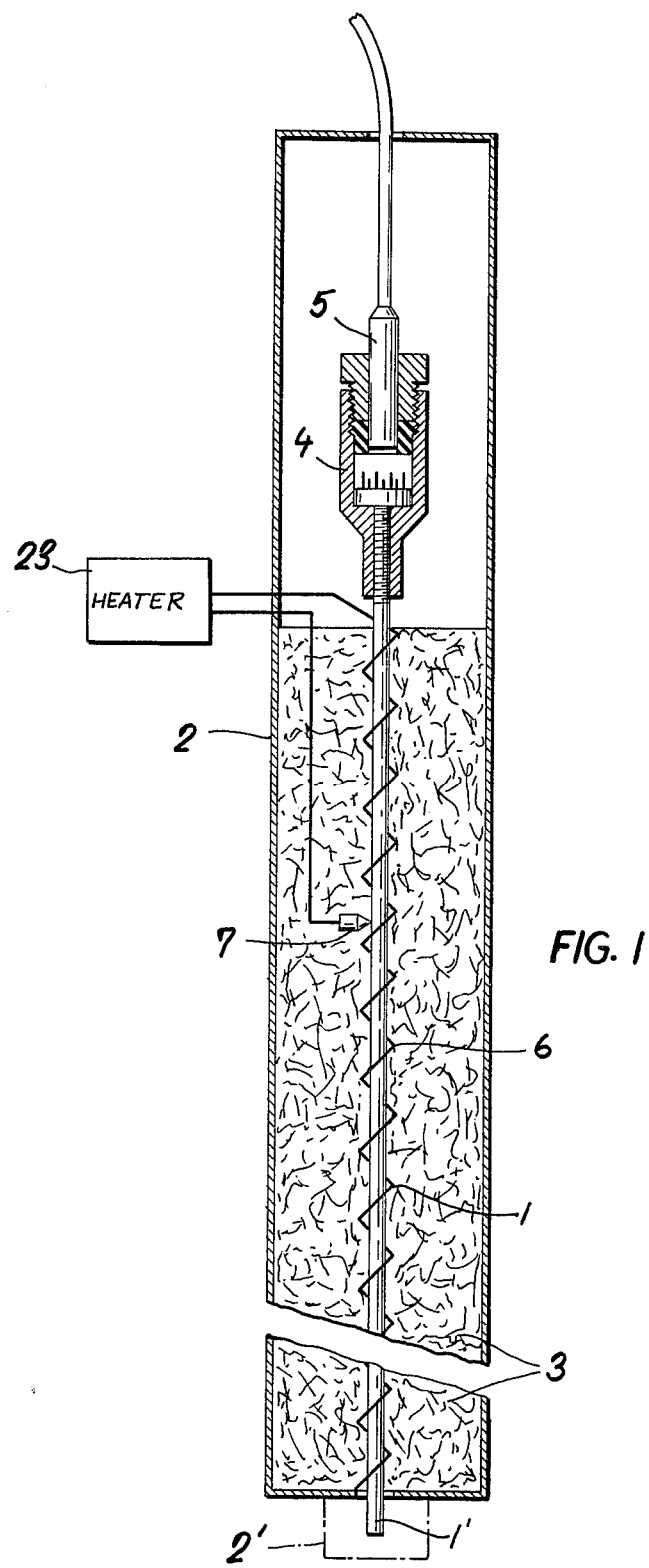
FIG. 1 is a longitudinal section through the probe according to this invention.

As shown in FIG. 1 an acoustic tube 1 made of copper is mounted in a sheet-metal sleeve 2 coaxial with tube 1 and slightly shorter than the tube 1 which is allowed to project from its end as shown at 1'. A mass 3 of glass-fiber insulating material supports the tube 1 within the tube 2. The tube 2 may be provided as shown in dot-dash lines at 2' with a guard protecting the end of the tube 1 and preventing entry therein of slag or the like.

A microphone 5 is mounted on the end of tube 1 remote from the end 1' means of a coupler 4. In addition an electric heating cable 6 connected to a heater 23 surrounds the tube 1 and maintains it at above 100° C. A thermostatic connection 7 also connected to the heater 23 maintains the temperature of this tube 1 constant.

Figure 3:
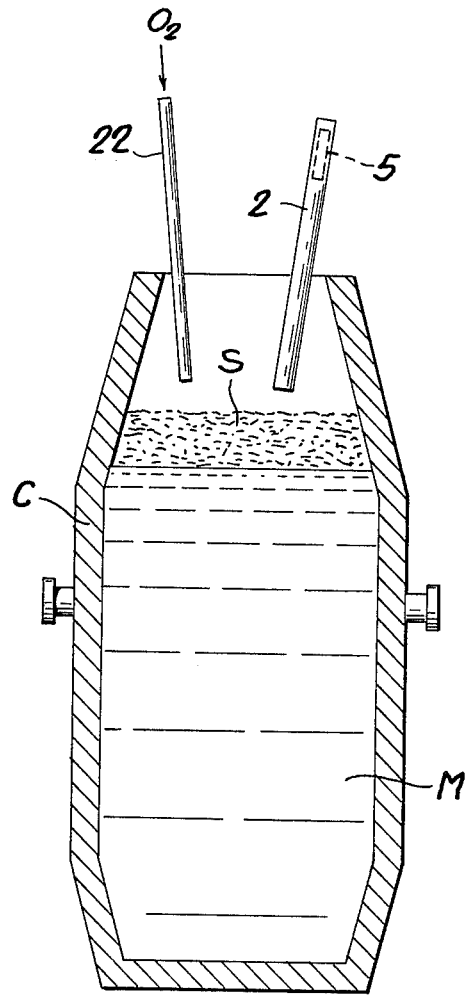
FIG. 3 is a large-scale view illustrating the use of the probe of FIG. 1.

In use as shown in FIG. 3 the probe formed by the microphone 5 and tubes 1 and 2 is directed into the mouth of a crucible C into which is also directed an oxygen lance 22. Within this crucible C is a body of molten steel M on which floats a layer of slag S. The slag S is sponge-like so that it absorbs a great deal of sound. Oxygen is blown in through the lance 22 at a constant pressure so that the amount of noise within the crucible C is determined by the amount of oxygen being pumped in and the amount of slag, as this slag absorbs much of the sound. The thicker the slag the less noise will be picked up by the microphone 5.

Figure 2:
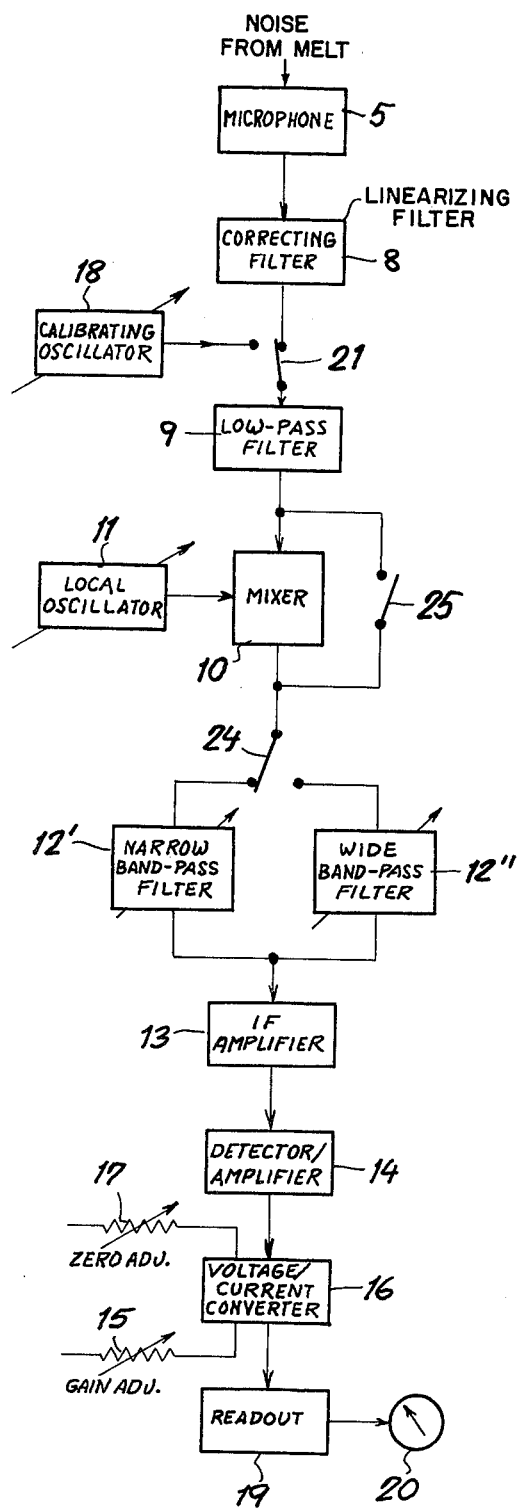
FIG. 2 is a block diagram illustrating the system in accordance with this invention.

The microphone 5 converts noise received into an electrical signal which as shown in FIG. 2 is passed through a correcting filter 8 being set up to compensate for the resonant frequency of the tube 1. Thereafter the corrected signal is fed through a low-pass filter which eliminates parasitic vibrations which are not in the range of interest.

After exiting from the low-pass filter 9 the signal is fed to a mixer 10 connected to a variable local oscillator 11 which beats the two signals together to form an intermediate-frequency signal that is fed through either of a pair of band-pass filters 12' or 12". The signal is then amplified in an IF amplifier 13 and fed to a detector/amplifier 14. Thereupon the signal is passed through a device 16 which changes its varying voltage into a varying current and feeds it to a readout 19 provided with a recording instrument or meter 20. The gain of the converter 16 may be adjusted by means of a potientometer 15 and a zero-adjusting potientometer 17 is also provided in this converter 16. The converter 16 changes the varying-voltage signal to a varying-current signal between 0 and 20 milliamperes.

At the start of each refining operation the apparatus is used as a frequency analyzer. To this end the switch 24 downstream from the mixer 10 is connected to put the narrow band-pass filter 12' in the circuit and the local oscillator 11 is varied until the meter 20 gives a strong output. The frequency is read off the local oscillator 11. It is also possible to block the local oscillator 11 and simply vary the narrow band-pass filter 12' to discover the characteristic frequency of the system being monitored. To this end the modulator 10 may be shunted by means of a switch 25.

A calibrating oscillator 18 may be connected upstream of the low-pass filter 9 by a switch 21 instead of the correcting filter 8 and microphone 5 in order to calibrate the arrangement.

Usually the narrow band-pass filter 12' is only used for the analysis of the spectrum. After the spectrum has been analyzed and a running monitoring of the operation is to be carried out the switch 24 is thrown to connect the wide band-pass filter 12" in its place. This wide band-pass filter 12" eliminates the need for constantly readjusting the device because the lining of the crucible C wears.

I claim:

1. In combination with a refining crucible holding a spongy slag-topped oxygen-refined iron melt, an apparatus for monitoring the spongy slag thickness during the refining operation in said crucible, said apparatus comprising:

an elongated acoustic tube having a predetermined resonant frequency and one end close to said slag and another end remote from said slag, means including a microphone at said end of said tube remote from said slag for detecting sound passing from said slag through said tube and converting said sound into an electrical signal, filter means connected to said microphone for linearizing said signal substantially in the range of said resonant frequency, and electrical heater means connected to said tube for continuously maintaining same at a temperature above ambient temperature.

2. The apparatus defined in claim 1, wherein said tube is maintained above 100° C by said heater means.

3. The apparatus defined in claim 1, further coprising a low-pass filter in addition to said filter means for eliminating from said signal all components having a frequency above a predetermined limit.

4. The apparatus defined in claim 2, further comprising local oscillator means and mixer means for heterodyning said electrical signal.

5. The apparatus defined in claim 4 wherein said local oscillator means is continuously variable.

6. The apparatus defined in claim 1, further comprising band-pass filter means in addition to the first-mentioned filter means indirectly connected to said microphone for receiving said electrical signal and filtering from said signal all components having a frequency above and below a predetermined range centered on the characteristic frequency of said crucible.

7. The apparatus defined in claim 6 wherein said band-pass filter means has a band width of 5 Hz.

8. A method of measuring the slag thickness of a spongy slag formed on the surface of an iron melt in a crucible, comprising the steps of:
generating a sound by directing a jet of oxygen against said slag in said crucible, thereby oxygen-refining said melt;
passing said sound from said crucible through an acoustic tube of predetermined resonant frequency having one end turned toward said slag and another end remote therefrom;
detecting said sound at the end of said tube remote from said slag and converting said detected sound into an electrical signal;
linearizing said electrical signal in the range of said resonant frequency; and
continuously electrically heating said tube to maintain it at a temperature above ambient temperature.

9. The method defined in claim 8 wherein said tube has a plurality of resonant frequencies, said sound being linearized over a frequency range encompassing several such resonant frequencies.

10. The method defined in claim 9 wherein said crucible has a characteristic frequency, said range encompassing said characteristic frequency.

11. The method defined in claim 10, further comprising the step of eliminating from said electrical signals all signals having a frequency above a predetermined frequency.

12. The method defined in claim 11, further comprising eliminating from said electrical signal all signals having a frequency above and below a predetermined frequency range centered on said characteristic frequency.

13. The method defined in claim 12 wherein said predetermined range has a band width of 60 Hz.

14. The method defined in claim 12, further comprising the step of mixing with said electrical signal another variable-frequency signal and beating said variable-frequency signal and said electrical signal together.

15. The method defined in claim 12, further comprising the step of displacing said predetermined range to determine said characteristic frequency.

* * * * *